United States Patent
Schmitt et al.

(10) Patent No.: US 6,888,465 B2
(45) Date of Patent: May 3, 2005

(54) SENSOR UNIT FOR DETECTING THE WETTING OF A WINDOW

(75) Inventors: Hans-Michael Schmitt, Muennerstadt (DE); Juergen Bach, Bad Neustadt (DE); Thomas Polzer, Bad Neustadt (DE); Rudolf Hartmann, Salz (DE)

(73) Assignee: Preh-Werke GmbH & Co. KG, Bad Neustadt a. d. Saale (DE)

( * ) Notice: Subject to any disclaimer, the term of this patent is extended or adjusted under 35 U.S.C. 154(b) by 0 days.

(21) Appl. No.: 10/281,363

(22) Filed: Oct. 28, 2002

(65) Prior Publication Data

US 2003/0080871 A1 May 1, 2003

(30) Foreign Application Priority Data

Oct. 26, 2001 (DE) .......................................... 101 52 998

(51) Int. Cl.$^7$ .............................................. G08B 21/00
(52) U.S. Cl. .................... 340/602; 340/604; 340/545.4; 318/483
(58) Field of Search ................................ 340/602, 604, 340/545.4; 200/574, 227.25, 341.8, 61.05, 61.04, 61.06; 318/483, DIG. 2

(56) References Cited

U.S. PATENT DOCUMENTS

| | | | | |
|---|---|---|---|---|
| 3,873,927 A | * | 3/1975 | Overall ........................ | 307/650 |
| 4,701,613 A | * | 10/1987 | Watanabe et al. ........... | 340/602 |
| 5,013,581 A | * | 5/1991 | Suhr et al. ................... | 427/569 |
| 5,402,075 A | * | 3/1995 | Lu et al. ...................... | 324/664 |
| 5,898,183 A | * | 4/1999 | Teder ........................... | 250/574 |
| 6,084,519 A | | 7/2000 | Coulling et al. | |
| 6,307,198 B1 | | 10/2001 | Asakura et al. | |
| 6,507,015 B1 | * | 1/2003 | Maeno et al. ........... | 250/227.25 |

FOREIGN PATENT DOCUMENTS

| | | |
|---|---|---|
| DE | 3721659 A1 | 1/1989 |
| DE | 3842180 A1 | 7/1989 |
| DE | 40 41 160 C2 | 7/1991 |
| DE | 691 15 647 T2 | 5/1992 |
| DE | 41 34 432 A1 | 4/1993 |
| DE | 9403135 U | 8/1994 |
| DE | 43 34 381 A1 | 4/1995 |
| DE | 44 24 985 A1 | 1/1996 |
| DE | 44 27 627 C2 | 2/1996 |
| DE | 0710593 A1 | 5/1996 |
| DE | 44 39 174 A1 | 5/1996 |
| DE | 19602354 A1 | 1/1997 |
| DE | 196 16 715 A1 | 11/1997 |
| DE | 693 15 452 T2 | 12/1997 |
| DE | 197 13 835 A1 | 10/1998 |
| DE | 197 23 858 A1 | 12/1998 |
| DE | 198 15 748 C2 | 10/1999 |
| EP | 0 556 682 A1 | 8/1993 |
| EP | 0 753 438 A1 | 1/1997 |
| JP | 403189590 A * | 8/1991 ................ 340/602 |
| JP | 9257952 | 10/1997 |
| WO | WO 90/05987 | 5/1990 |
| WO | WO 94/08247 A1 | 4/1994 |

* cited by examiner

*Primary Examiner*—Anh V. La
(74) *Attorney, Agent, or Firm*—Birch, Stewart, Kolasch & Birch, LLP

(57) ABSTRACT

The invention relates to a sensor unit for detecting the wetting of a window. Signals from the condensation sensor are used to control an air conditioning, heating, and/or ventilation unit. The signals of the rain sensor, on the contrary, are used to control a windshield wiper or washing unit for vehicles. A sensor unit, which comprises two sensors, is placed on the interior of the window. In a preferred variant, both are coupled to a common switchable evaluation unit, so that through mutual evaluation of the two sensors or their signals, both incipient condensation on the interior of a vehicle window and the wetting of the exterior, e.g., by rain, is detected. In an improvement of the invention, both sensors are integrated into a sensor module.

15 Claims, 2 Drawing Sheets

SENSOR UNIT FOR DETECTING THE WETTING OF A WINDOW

This nonprovisional application claims priority under 35 U.S.C. § 119(a) on Patent Application No. 101 52 998.8 filed in Germany on Oct. 26, 2001, which is herein incorporated by reference.

BACKGROUND OF THE INVENTION

1. Field of the Invention

The present invention relates to a sensor unit for detecting the wetting of a window, especially a vehicle windshield.

2. Description of the Background Art

Condensation sensors to detect internal moisture and rain sensors to detect external wetting of the window surface are known in the conventional art. In this case, signals from the condensation sensor are used to control an air conditioning, heating, and/or ventilation unit. The signals of the rain sensor, on the contrary, are used to control a windshield wiper or washing unit for vehicles. Sensors of this type operate, inter alia, according to the optoelectronic, resistive, or capacitive principle. Rain sensors are placed on the outside of the vehicle windshield, and condensation sensors on the interior side. Both operate independently from one another.

A sensor unit operating by the optoelectronic principle to detect external wetting is disclosed in DE 198 15 748 C2.

A device for the automatic control of a windshield wiper motor, which comprises a moisture sensor and an evaluation unit, is described in DE 43 34 381 A1. A rain sensor is also used in the device for operating a windshield wiper motor in DE 197 13 835 A1.

A method for adjusting the responsiveness of a precipitation sensor system to environmental conditions and a sensor system with a precipitation sensor are disclosed in DE 41 34 432 A1.

DE 6 9115647 T2 discloses a device for heating and ventilating the passenger compartment of a vehicle, in which a condensation sensor, placed on the interior side of a vehicle window, is connected to an electronic module to control closing valves.

DE 44 27 627 C2 discloses a method for the manufacture of a rain sensor working by the resistive measuring principle, said sensor which has at least two electrically conductive, adjacent sensor elements, which form an impedance of variable resistance, while working together with the electrically conductive substances wetting the sensor field, preferably water. The sensor consists substantially of two surfaces interlocking like fans, which are placed on a glass plate and form the resistance element.

Another moisture sensor for windshields is described in DE 40 41 160 C2. This sensor is placed on the exterior of the windshield and consists of two electrically conductive parts, which are at a distance from one another and are electrically insulated from one another by a gap of predefined width. The gap is preferably not greater than the width of a rain drop or fog droplet.

DE 44 24 985 A1 discloses a rain sensor, which has resistance structures placed on the vehicle window in the area of a windshield wiper, the structures change their resistance linearly, depending on the raindrops.

The construction and the mode of operation of a capacitive moisture sensor are disclosed in WO 94/08247.

The principle of the capacitive working moisture sensor is also described in EP 0 753 438 A1.

SUMMARY OF THE INVENTION

It is therefore an object of the present invention to provide a sensor unit, which simultaneously detects external, e.g., rain, and internal wetting, and which is cost-effective.

The invention is based on the idea of equipping the sensor unit with at least two sensors, both of which are placed on the interior of a window. In an embodiment of the invention, both sensors are coupled to a common switchable evaluation unit, so that through mutual evaluation of the two sensors both incipient condensation or incipient wetting on the interior of a vehicle window and also incipient wetting of the exterior of window, e.g., by rain, is detected.

In a preferred improvement of the invention, both sensors are integrated into a small-scale sensor module. The detection not desired in each case has no effect on the evaluation of the desired detection. In addition, measures can also be provided, for example, a capacitive shielding, by which the undesired effect is also prevented.

The sensors forming the sensor unit or integrated into the module, however, can also be operated with separate evaluation units.

The condensation sensor has a polymeric gold film, which responds to moisture, but can alternatively also have an interdigital structure with a glass cover layer.

The rain sensor is formed by a capacitative electrode structure in a nondifferential arrangement of the sensor surfaces.

In a further embodiment, a compact sensor module is provided through further integration of both sensors together with the common switchable unit. Other sensors, such as a driving light sensor, sun sensor, etc., can be easily integrated into this module.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION OF THE PREFERRED EMBODIMENTS

Figure 1:
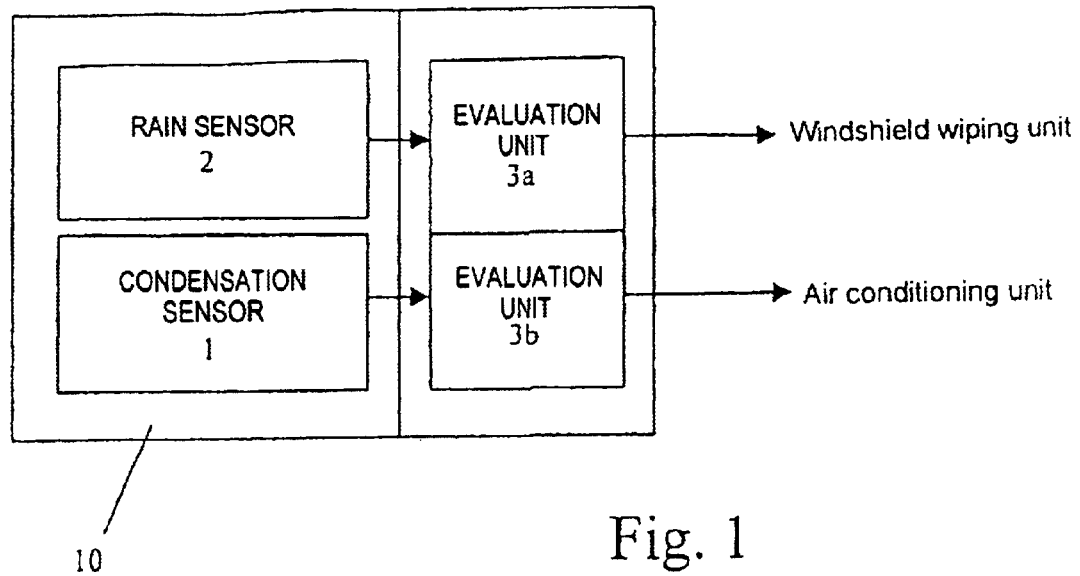
FIG. 1 is a window of a vehicle with an attached sensor unit.

FIG. 1 shows a general sensor unit 10, which comprises two separate sensors, a condensation sensor 1, and a rain sensor 2. Both sensors 1, 2 are electrically connected with an evaluation unit 3a or 3b, respectively. A common switchable evaluation electronic unit 3 can also be provided. The specific supply or signal lines are preferably integrated into a single structure.

The condensation sensor 1 works on a capacitive basis, whereby the capacitance of the condenser is changed by the moisture uptake of a polymer structure (not described) of the condensation sensor 1.

Figure 4:
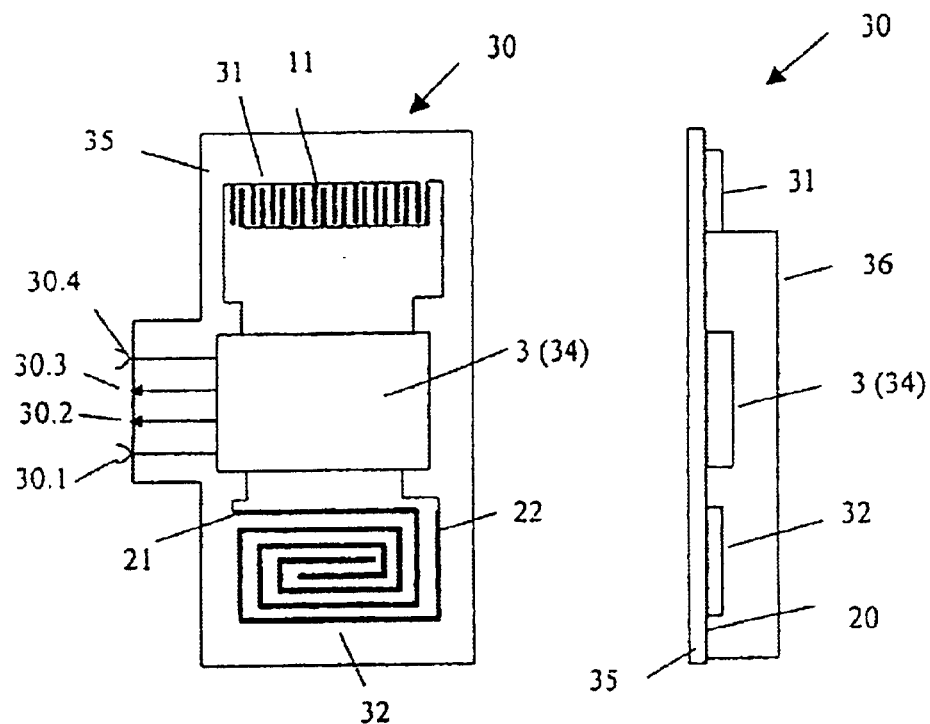
FIG. 4 is the internal structure of the sensor module.

The sensor surface of the rain sensor 2 includes two electrically separated conductive tracks 21, 22 (see FIG. 4). The capacitance of the rain sensor 2 is changed by the effect of the stray fields of these two conductive tracks 21, 22, working as condenser electrodes, e.g., by rain.

By switching the input of the evaluation unit 3 or through the individual evaluation units 3a and 3b, the specific signal of one of the two sensors 1, 2 is sent for evaluation, which is evaluated according to the programming. Because both sensors 1, 2 work on the same measuring principle, the evaluation is also the same as such.

The switching between the two sensors 1, 2 is not time-critical, because the reaction to the sensor signals can be long, compared with the switching and evaluation time.

Figure 2:
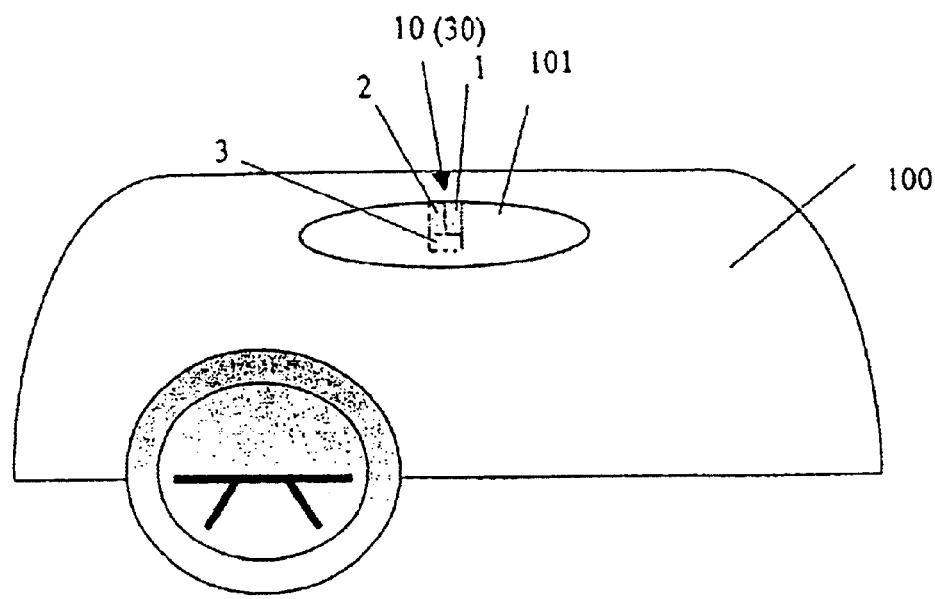
FIG. 2 is a block diagram of the sensor unit of FIG. 1.

The rain sensor 2 and the condensation sensor 1 are placed on the inside of a vehicle window 100 shown in FIG. 2, preferably within the area of a mirror base 101.

Figure 3:
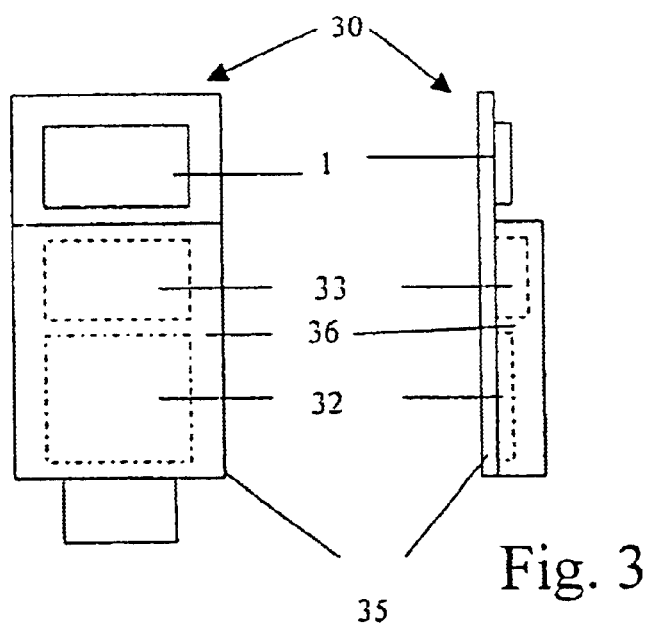
FIG. 3 is a general structure of a sensor module.

FIG. 3 shows as an advantageous design of a sensor module 30, which comprises both a condensation sensor 31 and a rain sensor 32, the signals of which are taken for evaluation via a common switchable evaluation unit 33, whereby in the preferred variant the entire evaluation unit 33 is a component of the sensor module 30. The condensation sensor 31 measures the internal condensation, and the rain sensor 32 the external moisture.

The sensor module 30 comprises a common supporting component 35, on which the condensation sensor 31 and the rain sensor 32 are placed together. The supporting component 35 is constructed so that it does not influence the function of the rain sensor 32 behind a vehicle window. The construction of the two sensors 31, 32 is as described in FIG. 1, for example. A shielding 36 is placed at least on the sensor surface 20 of the rain sensor 32. The shielding 36 prevents the moisture arising within the passenger compartment from affecting the rain sensor 32. It is also advantageous to place the shielding 36 over the evaluation unit 33.

An internal structure of the sensors 31 and 32 is shown in FIG. 4, whereby the condensation sensor 10 has an interdigital structure 10. Here, at least one part 34 of the evaluation unit 33, for example, switching electronics of the evaluation unit 33, is located on the supporting component 35, whereby the entire evaluation unit 33 can be integrated into the supporting component 35 (FIG. 3). The sensor module 30 can be connected to other electrical components over electrical connections 30.1 to 30.4.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A sensor unit for detecting the wetting of a window, comprising:

a first sensor for detecting internal wetting, the first sensor being located on the interior of the window; and a second sensor for detecting external wetting, and is placed on the interior of the window.

2. The sensor unit according to claim 1, wherein said first and second sensors are electrically connected to a common switchable evaluation unit, and wherein the sensor signal is connected to the evaluation unit whose signal is to be evaluated by the evaluation unit.

3. The sensor unit according to claim 1, wherein the sensor unit is constructed as a sensor module.

4. The sensor unit according to claim 3, wherein said first and second sensors are placed together on a supporting component of the sensor module.

5. The sensor unit according to claim 3, wherein components of at least one evaluation unit are located on a supporting component of the sensor module.

6. The sensor unit according to claim 1, wherein the internal wetting of the first sensor is detected by the direct capacitative measuring principle, and the external wetting of the second sensor is detected by the direct capacitative measuring principle.

7. The sensor unit according to claim 6, wherein the first sensor has a polymeric gold film.

8. The sensor unit according to claim 6, wherein the first sensor has an interdigital structure.

9. The sensor unit according to claim 6, wherein the second sensor has a capacitative electrode structure in a nondifferential arrangement of the sensor surfaces.

10. The sensor unit according to claim 1, wherein the first sensor is a condensation sensor, and the second sensor is a rain sensor.

11. A method for detecting interior and exterior wetting of a window, said method comprising the following steps:

detecting interior wetting of the window by a first sensor positioned on an interior surface of the window; and detecting, almost simultaneously, exterior wetting of the window by a second sensor positioned on the interior surface of the window, whereby an evaluation unit receives signals from said first sensor and said second sensor, makes an evaluation and outputs an output, dependent on the evaluation.

12. A sensor unit being mounted to a first surface of a window, the sensor unit comprising:

a condensation sensor for detecting wetting of the first surface; and a rain sensor for detecting wetting of a second surface of a window, wherein the first surface and the second surface of the window are substantially parallel to one another.

13. The sensor unit according to claim 12, wherein the condensation sensor provides signals to the sensor unit for control of air conditioning, heating, or ventilation.

14. The sensor unit according to claim 12, wherein the rain sensor provides signals to the sensor unit for control of at least one windshield wiper.

15. The sensor unit according to claim 12, wherein the window is used in a vehicle.

* * * * *